United States Patent [19]
Belfer et al.

[11] Patent Number: 6,142,170
[45] Date of Patent: Nov. 7, 2000

[54] APPARATUS AND METHOD FOR DISPENSING DISINFECTANT COMPOSITIONS FOR DISINFECTING WATER SYSTEMS AND LINES

[76] Inventors: William A. Belfer, 804 W. Park Ave.; Phillip J. Petillo, 1206 Herbert Ave., both of Ocean Township, N.J. 07712

[21] Appl. No.: 09/047,550

[22] Filed: Mar. 25, 1998

[51] Int. Cl.⁷ .................................................. B08B 9/027
[52] U.S. Cl. .......................... 137/240; 134/30; 134/94.1; 134/95.1; 134/99.1; 134/102.2; 134/169 C; 134/171; 137/624.11; 137/624.13; 137/899; 222/148; 312/209
[58] Field of Search ..................................... 137/240, 241, 137/624.11, 624.13, 624.18, 899; 134/26, 30, 94.1, 95.1, 95.2, 99.1, 100.1, 102.1, 102.2, 102.3, 167 C, 169 C, 169 R, 171; 222/129, 132, 135, 144.5, 148, 504; 433/80, 98; 312/209

[56] References Cited

U.S. PATENT DOCUMENTS

| | | | |
|---|---|---|---|
| 4,892,112 | 1/1990 | Knetsch | 137/240 |
| 5,013,240 | 5/1991 | Bailey et al. | 433/98 |
| 5,526,841 | 6/1996 | Detsch et al. | 222/148 |
| 5,538,423 | 7/1996 | Coss et al. | 433/98 |
| 5,709,546 | 1/1998 | Waggoner | 433/82 |

*Primary Examiner*—George L. Walton
*Attorney, Agent, or Firm*—Ezra Sutton

[57] ABSTRACT

In accordance with the present invention, there is provided an asepsis dispenser apparatus for dispensing disinfectant solutions for cleansing and decontaminating the contaminated surfaces of dental, food and medical equipment, which equipment is connected to a water source by a water inlet line. The asepsis dispenser apparatus includes a housing having an interior compartment for holding in place first and second storage canisters, containing a first disinfectant composition and a second disinfectant composition. The asepsis dispenser apparatus further includes a two-way solenoid valve connected to both of the first and second storage canisters, and a three-way solenoid valve connected to the three-way solenoid valve, wherein the three-way solenoid valve is for controlling the water source supplied to the water inlet line which is connected to the dental, food or medical equipment. In addition, the asepsis dispenser apparatus includes a programmable timing controller device for opening and closing the solenoid valves in order to control the first and second storage canisters for supplying the first disinfectant composition or the second disinfectant composition to the contaminated surfaces; and a 9 volt battery power supply for supplying electrical power to both solenoid valves and to the programmable timing controller device.

18 Claims, 7 Drawing Sheets

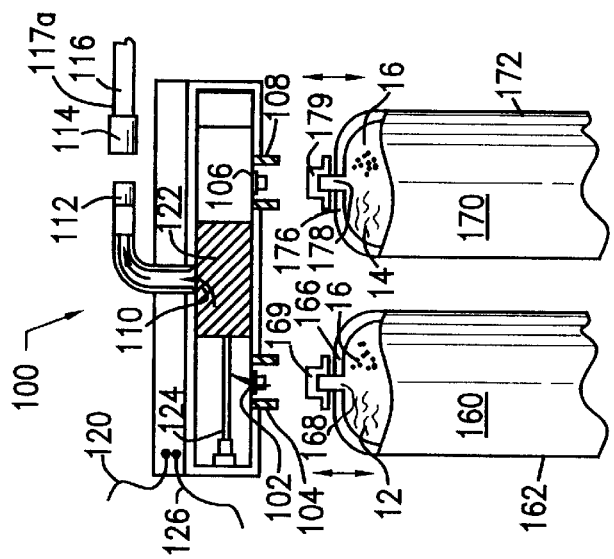
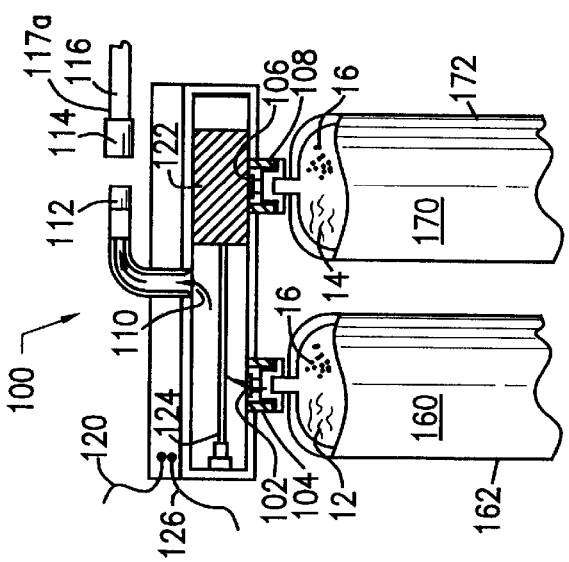
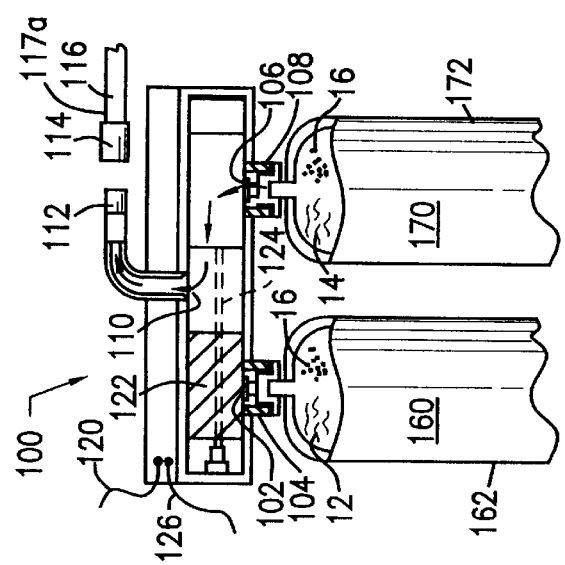

APPARATUS AND METHOD FOR DISPENSING DISINFECTANT COMPOSITIONS FOR DISINFECTING WATER SYSTEMS AND LINES

FIELD OF THE INVENTION

This invention relates to an asepsis dispenser apparatus and method for dispensing a disinfectant composition for the cleansing and decontamination of the biofilm and microbial contaminants within water systems and water lines used in medical and dental facilities. More particularly, this dispensing asepsis apparatus will destroy or inactivate viruses, bacteria, funguses, and parasites on contact; and is easy to use, safe, non-flammable, and environmentally compatible.

BACKGROUND OF THE INVENTION

The American Dental Association Council on Scientific Affairs recommended in December 1995 that industry and the research community undertake an aggressive and ambitious product development program to improve the water quality from dental units. It declared that by the year 2000, water delivered to patients during non-surgical dental procedures should consistently contain no more than 200 colony forming units per milliliter of aerobic mesophilic heterotrophic bacteria at any point in time in the unfiltered output of the dental unit. The impetus for the ADA statement was the concern in the scientific community about the rising incidence of infectious disease among patient populations, the high incidence of immuno-compromised patients that dentists were treating, and the realization that water coming from dental units is less than the standard for potable drinking water. The potential for cross-contamination existed and there was fear that patients were being subjected to risk during routine dental procedures. Research showed that there were two causes of bacterial contamination in the dental water lines. The first was the persistence of biofilm, a build-up of bacterial colonies (plaque) which adhered to walls of the tubing. The other was back-flow of bacterial laden fluids from the dental handpieces and water syringes, a result of reversal pressures or diffusion or backgrowth of the bacterial contaminants. It has been long known that Legionella pneumophila, the infective agent of Legionnaire's disease, was prevalent in contaminated water supplies. However, a most alarming report was that dental professionals had a significant occupational exposure to Legionella from aerosolization of dental unit water. This was confirmed by the high levels of anti-Legionella antibodies found in their blood. A mild, self-limiting form of Legionella disease, Pontiac fever, was the most common illness. But, there is one report of a dentist who died after contracting Legionella pneumonia from his own contaminated dental waterlines. Based on these facts, the implications for public health are very serious.

To date there have been few viable solutions to this problem. Biofilm is resistant to removal and the agents that have been used are either caustic, corrosive, toxic or damaging to patients, staff personnel, equipment or the environment. The remedies that are available are either not completely effective or they damage dental devices, dental components and parts, and/or dental water units.

Aside from the ADA there are regulatory agencies that are involved in this issue. The Occupational Safety and Health Agency (OSHA) has proposed regulations which require the elimination of hazardous bio-aerosols in the workplace, including dental offices. Because of the prevalence of Legionella in dental water lines, OSHA pressure will cause a strong demand for a solution to the problem. Moreover, as media focus becomes more acute, public awareness will stimulate the dental profession to introduce new systems and protocols for waterline decontamination.

The Food and Drug Administration (FDA) has already cleared several devices for water line contamination. They are enabling rapid review and clearance of new products under the 510(k) filing process.

There remains a need for an improved asepsis apparatus and method for the dispensing of a disinfectant solution safely in order to clean and decontaminate the biofilm and the microbial contaminants within water, air and vacuum systems, as well as water, air and vacuum lines in dental and medical systems. Additionally, the asepsis apparatus should easily and automatically supply a predetermined amount of disinfectant solution to the dental equipment (i.e. water system) during the non-working hours (night time) at the dental facility.

DESCRIPTION OF THE PRIOR ART

Sanitizing systems, cleaning systems, cleaning apparatuses for liquid delivery devices having various designs, configurations, structures and materials of construction have been disclosed in the prior art. For example, U.S. Pat. No. 5,709,546 discloses a water sanitizing system for the provision of sanitized water for human consumption in the use of medical and dental devices using hydroxycarboxylic acid. This prior art patent does not disclose the structure of the asepsis dispenser apparatus of the present invention.

U.S. Pat. No. 5,419,346 discloses an automated flushing module with the capability of performing an internal cleansing of internally soiled components of a patient support apparatus. This prior art patent does not disclose the structure of the asepsis dispenser apparatus of the present invention.

U.S. Pat. No. 5,351,892 discloses a dispensing apparatus having the capability to select, dilute, mix and dispense multiple solutions, liquids and semi-liquids, such that this dispensing apparatus can be used in combination with a shower, washing machine, dishwasher, food vending machine, medical device, etc. This prior art patent does not disclose the structure of the asepsis dispenser apparatus of the present invention.

U.S. Pat. No. 4,497,334 discloses a cleansing apparatus for liquid delivery systems in dental facilities. This prior art patent does not disclose the structure of the asepsis dispenser apparatus of the present invention.

None of the prior art patents teach or disclose the structure and configuration of the asepsis dispenser apparatus of the present invention that includes one or more pressurized disinfectant solution canisters connected to a two-way solenoid valve, a three-way solenoid valve being connected to the two-way solenoid valve via a disinfectant solution transfer line where the three-way solenoid valve controls the water source of a water inlet line to dental equipment; and having a programmable timing controller device for opening and closing the solenoid valves in order to control the one or more canisters containing disinfectant solutions therein for supplying the disinfectant solutions to contaminated surfaces of the dental equipment.

Accordingly, it is an object of the present invention to provide an asepsis apparatus for dispensing a disinfectant composition for the cleansing and decontamination of the biofilm and microbial contaminants within water systems and to the water and air lines used in medical and dental facilities.

Another object of the present invention is to provide an asepsis apparatus for safely and automatically supplying a disinfectant composition which, when applied to the contaminated internal surfaces of the water system and its air and water lines/tubes, the disinfectant will kill or inactivate viruses, bacteria, funguses, and parasites on contact.

Another object of the present invention is to provide an asepsis apparatus that is adaptable to any new or used dental chair system by any manufacturer such that the small and unobtrusive asepsis apparatus can be easily and quickly installed by the practitioner.

Another object of the present invention is to provide an asepsis apparatus that operates on a 9 volt battery having no electrical connections (to a wall electrical outlet).

Another object of the present invention is to provide an asepsis apparatus that is easy to use and there is no servicing required, such that by a touch of a button the asepsis apparatus will initiate a self-contained timer which will deliver a correct volume of disinfectant composition/ solution to the dental water system and its air and water lines for an appropriate cleaning and decontamination procedure.

Another object of the present invention is to provide an asepsis apparatus for automatically supplying a predetermined amount of disinfectant solution for the decontamination and cleaning of the dental equipment (i.e. water system and its water and air lines, during the non-working hours (night time) at the dental facility.

Another object of the present invention is to provide an asepsis apparatus that prevents back flow from dental handpieces, syringes, and back pressure vapor contamination from suction lines, such that the resultant water and air purity is well below the recommended 200 CFU/liter, established by the Centers for Disease Control and Prevention, after the cleaning and decontamination by the disinfectant composition which chemically disinfects, filters and scrubs the biofilm from the water and air lines of any dental water system.

Another object of the present invention is to provide an asepsis apparatus that includes a self-charging system being easily applied to the dental water system and where no leaking of the asepsis apparatus occurs when left unattended.

Another object of the present invention is to provide a asepsis apparatus having disposable components therein and still operates at a low cost of utilization for parts and disinfectant solution.

Another object of the present invention is to provide an asepsis apparatus that has a low cost of manufacturing and having a minimal amount of components; and is durable, safe and reliable in operation without causing damage to the water system and its air and water lines being cleaned and decontaminated.

A further object of the present invention is to provide an asepsis apparatus that may be mass produced in an automated and economical manner and is readily affordable by the practitioner.

SUMMARY OF THE INVENTION

In accordance with the present invention, there is provided an asepsis dispenser apparatus for dispensing disinfectant solutions for cleansing and decontaminating the contaminated surfaces of dental, food and medical equipment, which equipment is connected to a water source by a water inlet line. The asepsis dispenser apparatus includes a housing having an interior compartment for holding in place first and second storage canisters. The first storage canister contains a first disinfectant composition, and the second storage canister contains a second disinfectant composition. The asepsis dispenser apparatus includes a two-way solenoid valve being connected to both of the first and second storage canisters, and a three-way solenoid valve being connected to the two-way solenoid valve, wherein the three-way solenoid valve controls the water source being supplied to the water inlet line which is connected to the dental, food or medical equipment. In addition, the asepsis dispenser apparatus includes a programmable timing controller device for opening and closing the solenoid valves in order to control the first and second storage canisters for supplying the first disinfectant composition or the second disinfectant composition to the contaminated surfaces; and a 9 volt battery power supply for supplying electrical power to both solenoid valves and to the programmable timing controller device.

BRIEF DESCRIPTION OF THE DRAWINGS

Further objects, features, and advantages of the present invention will become apparent upon consideration of the detailed description of the presently-preferred embodiments, when taken in conjunction with the accompanying drawings wherein:

FIG. 2a is an enlarged cross-sectional view of the asepsis dispenser apparatus of the present invention taken along lines 2—2 of FIG. 1 showing the first three-way solenoid valve in operational use in which the flavored hydrogen peroxide solution from the second canister is being supplied under pressure through the second inlet opening of the first three-way solenoid valve;

FIG. 2b is an enlarged cross-sectional view of the asepsis dispenser apparatus of the present invention taken along lines 2—2 of FIG. 1 showing the first three-way solenoid valve in operational use in which the disinfectant composition from the first canister is being supplied under pressure through the first inlet opening of the first three-way solenoid valve;

FIG. 2c is an enlarged cross-sectional view of the asepsis dispenser apparatus of the present invention taken along lines 2—2 of FIG. 1 showing the first three-way solenoid valve in operational use such that the first and second canisters are detachably connected to the first three-way solenoid valve and the three-way solenoid valve is in a closed position;

DETAILED DESCRIPTION OF THE PREFERRED EMBODIMENT

Figure 1:
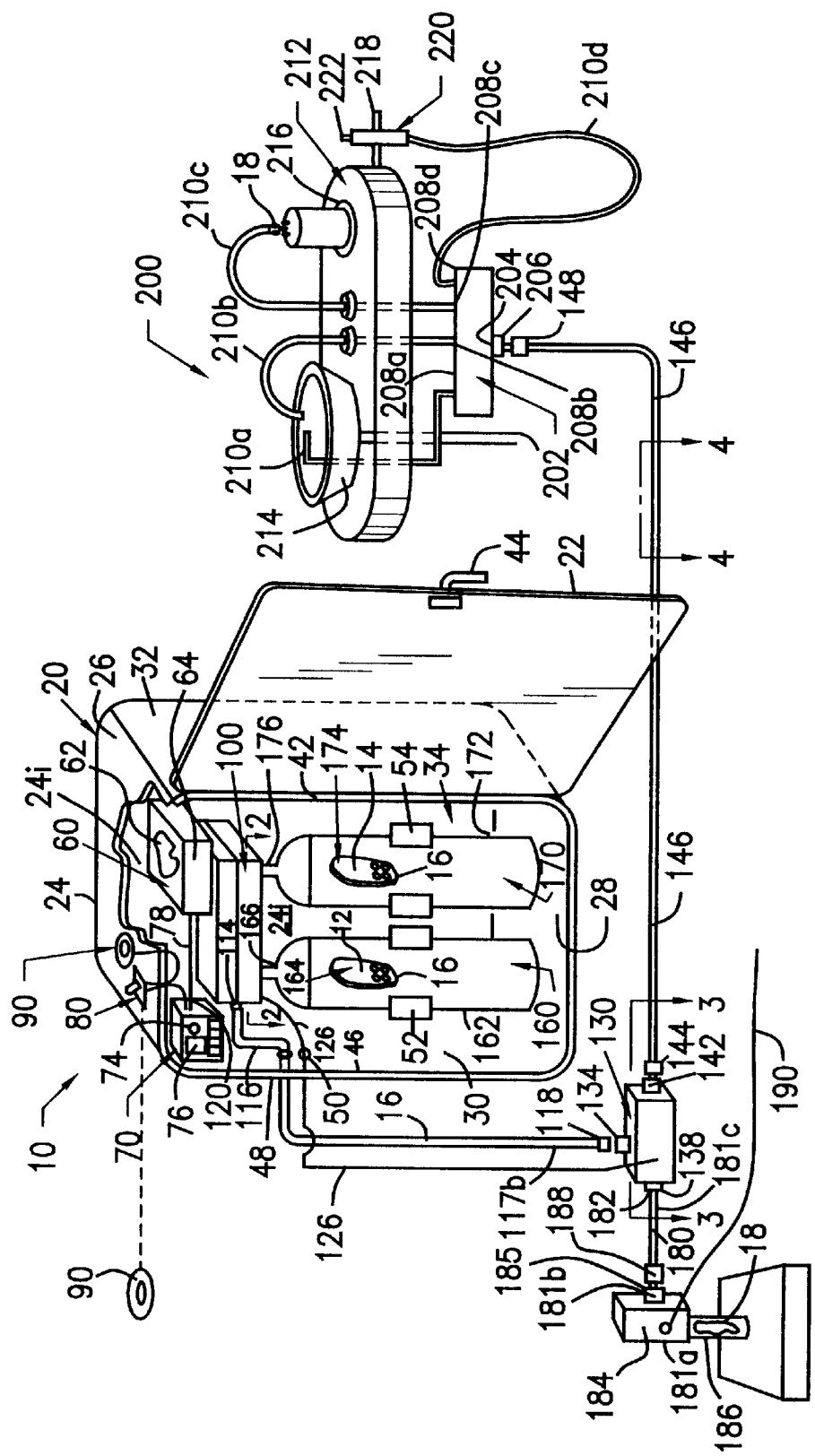
FIG. 1 is a front perspective view of the asepsis dispenser apparatus of the preferred embodiment of the present invention showing the major component parts contained therein, and in operational use to cleanse and sanitize a dental water system and its water transfer service lines.

The asepsis dispenser apparatus 10 and its component parts of the preferred embodiment of the present invention are represented in detail by FIGS. 1 through 5 of the drawings. The asepsis dispenser apparatus 300 and its component parts of the alternate embodiment of the present invention are represented in detail by FIG. 6 of the drawings. The method 400 of the cleansing and sanitizing procedure for the removal of biofilm accumulation 13 and destruction of pathogenic and non-pathogenic microorganism 15 within the water system 200 and its water transfer service lines 146, 210a to 210d having various operational steps performed in the cleansing and sanitizing process is disclosed in the preferred embodiment of the present invention and is represented in detail by FIGS. 7A and 7B of the drawings. The asepsis dispenser apparatus 10 is used for dispensing one or more disinfectant solutions 12 and 14 in order to cleanse and sanitize biofilm accumulation 13 and microbial contaminants 15 from interior and exterior surfaces of the water system 200 and its water transfer lines and tubes 146, 210a, 210b, 210c and 210d. The method 400 of cleansing and sanitizing the biofilm accumulation 13 and microbial contaminants 15 from interior and exterior surfaces of the water system 200 and its water transfer service lines 146, 210a to 210d is fully explained in the "Operation of the Present Invention" section.

The asepsis dispenser apparatus 10 includes a dispenser housing 20 having a substantially rectangular configuration with an interior compartment/chamber 34 for holding in place a housing 60 having a battery compartment 62 for a battery 66 or power supply (AC or DC), a programmable electronic cycle timer device 70, and a pair of pressurized aerosol canisters 160 and 170 having a three-way solenoid valve 100 being connectably attached to both of the pressurized aerosol canisters 160 and 170, respectively. The asepsis dispenser apparatus 10 further includes a daytime/nighttime switch 80, a start-up switch 90 and a three-way solenoid valve 130. The pair of pressurized aerosol canisters 160 and 170 are used for holding a first disinfectant composition 12 and a second disinfectant composition 14 being a flavored hydrogen peroxide solution. The first disinfectant composition 12 includes a variety of germicidal and cleansing ingredients as identified in copending patent application Ser. No. 09/047,570 and incorporated herein by reference.

Dispenser housing 20, as shown in FIG. 1 of the drawings, includes a front door 22, a rear wall 24, a top wall 26, a bottom wall 28, and side walls 30 and 32, all being integrally connected to form a substantially rectangular configuration which forms an interior compartment area 34 for holding in place the aforementioned battery housing 60, cycle timer device 70 and pressurized aerosol canisters 160 and 170. Dispenser housing 20 can be made of plastic or metal for ease of cleaning. In addition, dispenser housing 20 can be placed in a dental chair, or within the closet control panel on the dental chair, or housing 20 can be remotely located.

As shown in FIG. 1, front door 22 includes a hinge member 42 being attached to the left side wall 30, a door handle 44 being centrally located at front door edge 22e and a door latch 46 being attached to the right side wall 32. Interior rear wall surface 24i of rear wall 24 of dispenser housing 20 includes a pair of first and second unshaped canister clips 52 and 54 being attached thereon and for holding in place the first and second pressurized aerosol canisters 160 and 170, respectively. Interior rear wall 24i also includes the housing 60 attached thereon for a power supply or battery 66; and the electronic cycle timer device 70 also attached thereon. Top wall 26 includes a daytime/nighttime switch 80 attached thereon, as well as the start-up switch 90 also attached thereon. Start-up switch 90 can also be remotely located and connected via electrical line 94. Top wall 26 further includes hole openings 88 and 96 for receiving therein electrical lines 86 and 94 of the daytime/nighttime switch 80 and start-up switch 90, respectively. Side wall 30 includes an upper hole opening 48 for receiving therein the outlet transfer line 116 from three-way solenoid valve 100.

Housing 60, for the power supply or battery 66, as shown in FIG. 1, includes a compartment 62 having a compartment cover 64, such that compartment 62 holds in place a 9 volt nickel cadium battery 66. Compartment 62 also includes an attachment clip 67 having a positive ($^+$) pole connector 68p and having a negative (−) pole connector 68n thereon. Battery 66 is electrically connected to the electronic cycle timer device 70 via electrical line 78, as shown in FIGS. 1 and 5 of the drawings.

Figure 5:
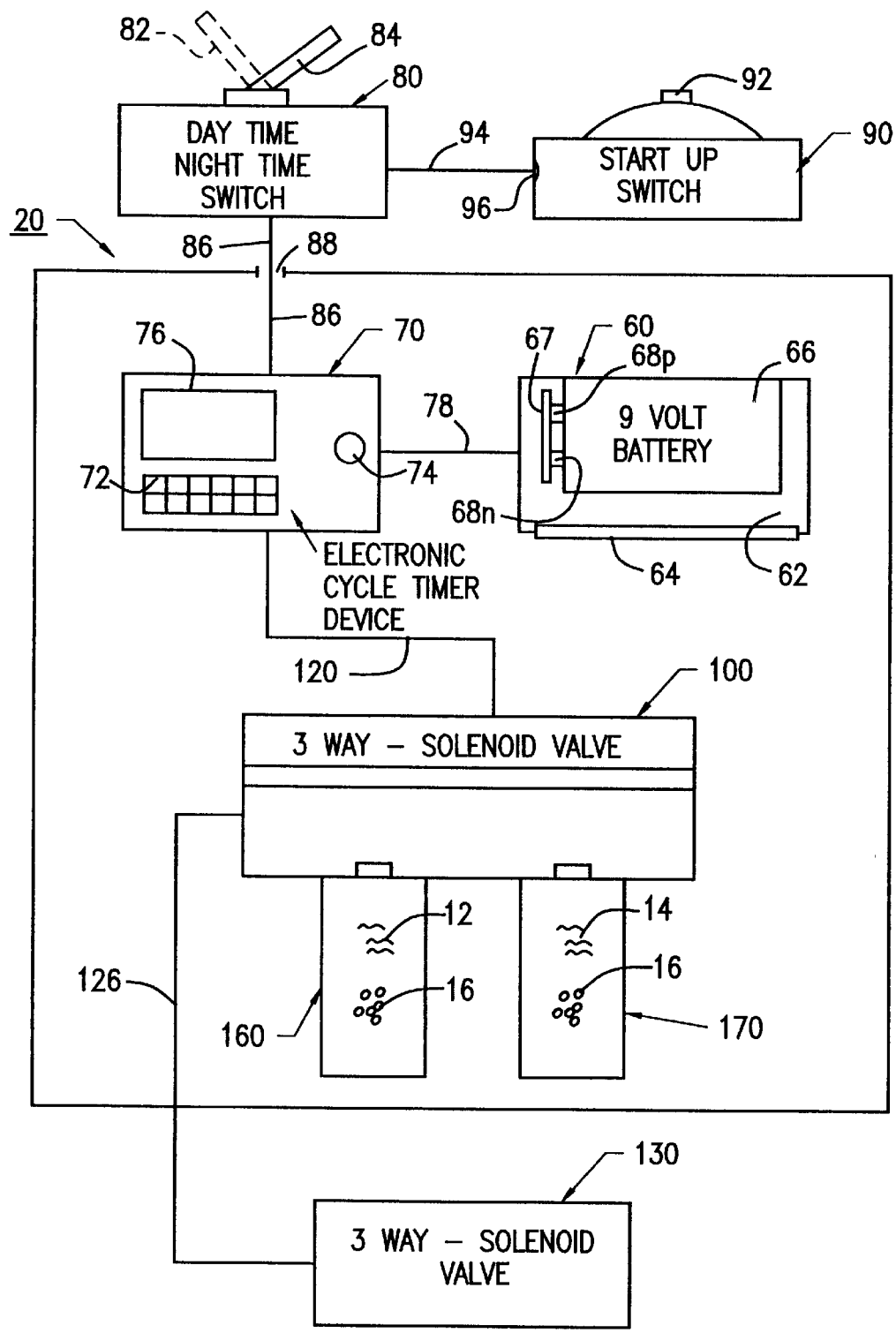
FIG. 5 is an electrical schematic block diagram of the asepsis dispenser apparatus of the present invention showing the electrical connections of the major components parts therein.

The programmable electronic cycle timer device 70, as shown in FIGS. 1 and 5, includes a programmable timing controller member 72 for programming via keyboard 73 the length of time that a specified amount of disinfectant compositions 12 or 14 is discharged from the first or second pressurized aerosol canisters 160 and 170. In place of programmable timing controller member 72, a preprogrammed micro-chip (not shown) may be used for controlling the specified amounts of disinfectant compositions 12 or 14 to be dispensed. This micro-chip may be installed by the manufacturer. Cycle timer device 70 further includes a selector knob 74 for indicating which pressurized aerosol canister 160 or 170 is to be used for discharging a specified amount of disinfectant composition 12 or 14 via the three-way solenoid valve 100, a visual display screen 76 for positively indicating the specified amount of disinfectant composition 12 or 14 to be discharged from the pressurized aerosol canisters 160 and 170 via the three-way solenoid valve 100, and an electrical line 78 connected to the battery source 66 for powering electronic cycle timer device 70.

Daytime/nighttime switch 80, as shown in FIG. 1 of the drawings, includes a daytime position 82 and a nighttime position 84 for electronically indicating which pressurized aerosol canister 160 or 170 is to be discharged via the programmable electronic cycle timer device 70, and an electrical line 86 connected to the electronic cycle timer device 70 for transferring the signal. Daytime/nighttime switch 80 is electrically connected to the programmable electronic cycle timer device 70 via electrical line 85, as shown in FIGS. 1 and 5 of the drawings.

Start-up switch 90 includes an initiating sequence button 92 and an electrical line 94. Start-up switch 90 is electrically connected to the daytime/nighttime switch 80 via electrical line 94, as shown in FIGS. 1 and 5 of the drawings.

The three-way solenoid valve 100, as shown in FIGS. 1, 2 and 5 of the drawings, includes a first inlet opening 102 having a first connector member 104 being a quick disconnect female coupling, a second inlet opening 106 having a second connector member 108 being a quick disconnect female coupling, and an outlet opening 110 having an outlet connector member 112 being a quick disconnect female coupling. Three-way solenoid valve 100 further includes an internal movable valve stop member 122 having a shaft 124 thereon for the lateral movement of stop member 122. In addition, three-way solenoid 100 includes an electrical line 120 electrically connected to the electronic cycle timer device 70 and an electrical line 126 electrically connected to the three-way solenoid valve 130, as shown in FIG. 1, 3 and 5 of the drawings. Three-way solenoid valve 100 also includes an outlet transfer line 116 having at each end 117a and 117b a pair of quick disconnect male couplings 114 and 118, respectively. Transfer line 116, connects the three-way solenoid valve 100 to the three-way solenoid valve 130, such that outlet female coupling 112 of three-way solenoid valve 100 is detachably connected to male coupling 114 at end 117a of outlet transfer line 116, and at the other end 117b of outlet transfer line 116 male coupling 118 is detachably connected to the female coupling 134 of the three-way solenoid valve 130, as shown in FIGS. 1 and 3 of the drawings.

Three-way solenoid valve 130, as shown in FIGS. 1, 3 and 5 of the drawings, includes a first inlet opening 132 having a first connector member 134 being a quick disconnect female coupling, a second inlet opening 136 having a second connector member 138 being a quick disconnect female coupling, and an outlet opening 140 having an outlet connector member 142 being a quick disconnect female coupling. Three-way solenoid valve 130 further includes an internal rotatable valve member 152 having first and second valve open positions 154 and 156 thereon. As previously mentioned, three-way solenoid valve 130 is electrically connected to three-way solenoid valve 100 via electrical line 126.

A first pressurized aerosol canister 160 includes a cylindrical cylinder housing 162 having an interior chamber 164 for holding disinfectant composition 12 and compressed air 16 therein, a tapered neck 166 having a nozzle opening 168 and a connector member 169 being a quick disconnect male coupling thereon for attaching to the quick disconnect female coupling 104 of three-way solenoid valve 100.

A second pressurized aerosol canister 170 includes a cylindrical cylinder housing 172 having an interior chamber 174 for holding the flavored hydrogen peroxide solution 14 and compressed air 16 therein, a tapered neck 176 having a nozzle opening 178 and a connector member 179 being a quick disconnect male coupling thereon for attaching to the quick disconnect female coupling 108. The three-way solenoid valve 100 is physically and mechanically connected to both of the quick disconnect male couplings 169 and 179 of both of the first and second pressurized aerosol canisters 160 and 170, respectively, via the quick disconnect female couplings 104 and 108, respectively, of three-way solenoid valve 100.

In the preferred embodiment, storage canisters 160 and 170 are pressurized with sterile compressed air, carbon dioxide, nitrogen or helium. However, non-pressurized vessels would also work in this invention, by using them in combination with pumps to deliver the compositions 12 and 14. Alternatively, syringes may be used to deliver the compositions directly to the lines without using canisters, vessels or pumps.

Figure 3A:
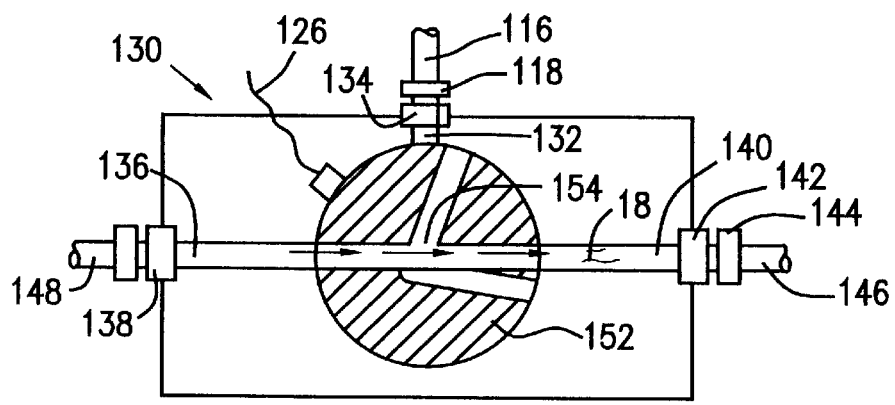
FIG. 3a is an enlarged cross-sectional view of the asepsis dispenser apparatus of the present invention taken along lines 3—3 of FIG. 1 showing the second three-way solenoid valve in operational use in which the internal rotatable valve member is in its first valve open position for allowing fresh water from the main water supply line to flow through the second three-way solenoid valve and to the water system and its water transfer service lines.
Figure 3B:
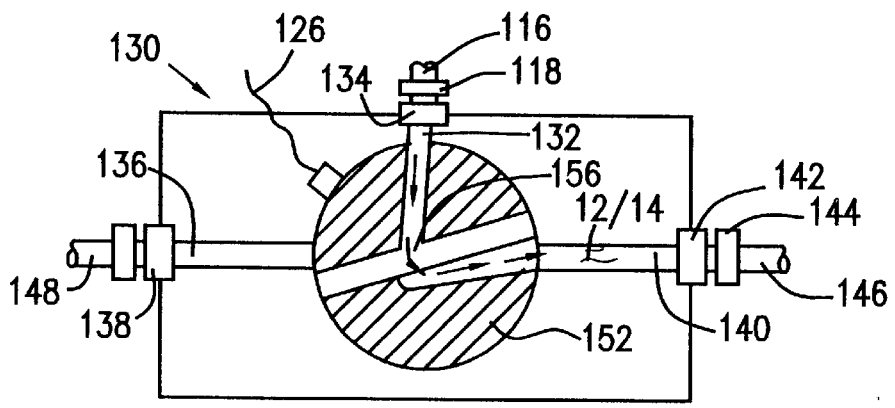
FIG. 3b is an enlarged cross-sectional view of the asepsis dispenser apparatus of the present invention taken along lines 3—3 of FIG. 1 showing the second three-way solenoid valve in operational use in which the internal rotatable valve member is in its second valve open position for allowing disinfectant composition or hydrogen peroxide solution to flow through the second three-way solenoid valve and to the water system and its water transfer service lines.

Externally located, the three-way solenoid valve 130 having the quick disconnect female coupling 138 is attached to the quick disconnect male coupling 182 of the inlet water transfer line 180, as shown in FIGS. 1, 3a and 3b of the drawings. Additionally, an automatic ball valve 184 is attached at one end 181a to the main incoming water line 186, and at the other end 181b of automatic ball valve 184 there is a quick disconnect female coupling 185 thereon attached to the quick disconnect male coupling 188 of inlet water transfer line 180. Automatic ball valve 184 is electrically connected to the water system 200 via electrical line 190. Electrical line 190 is used for activating the automatic ball valve 184 to an open position which lets the supply water 18 from the main incoming water line 186 flow through the water transfer line 180, the three-way solenoid valve 130 and water transfer line 146, respectively, to the water system 200 and its water service lines 210a to 210d.

The electrical schematic block diagram, as shown in FIG. 5 of the drawings, for asepsis dispenser apparatus 10 of the present invention depicts the electrical connections of the component parts. The power source 66 (9 volt battery or power supply) is electrically connected to the programmable electronic cycle timer device 70 via electrical line 78. Cycle timer device 70 is electrically connected to both the daytime/nighttime switch 80 and the three-way solenoid valve 100 via electrical lines 86 and 120, respectively. Daytime/nighttime switch 80 is electrically connected to the start-up switch 90 having an initiating sequence button 92 thereon via electrical line 94. Three-solenoid valve 100 is electrically connected to the three-way solenoid valve 130 via electrical line 126.

Water system 200, as shown in FIG. 1, includes a manifold member 202 having an inlet opening 204 with a connector member 206 therein. The connector member 206 is a quick disconnect female coupling. Manifold member 202 further includes a plurality of outlet openings 208a to 208d having a plurality of water service transfer tubes/lines 210a to 210d. Water system 200 further includes a base member 212 having a water receiving receptacle/bowl 214 thereon for receiving water service transfer tubes 210a and 210b thereon, and having a cup holding member 216 for receiving water service transfer tube 210c. Base member 212 further includes a holding clip 218 for holding in place a water spray handpiece 220 having a nozzle member 222. Nozzle member 222 is attached to the water service transfer tube 210d.

Water transfer line 146 having quick disconnect male coupling 148 is attached to the quick disconnect female coupling 206 of the manifold member 202 of water system 200. When asepsis dispenser apparatus 10 is in the operational mode, water transfer line 146 is able to receive either the disinfectant composition 12 or flavored hydrogen peroxide solution 14 in order to cleanse and sanitize the water system 200, its component parts 202, 214, 216 and 222 and its transfer lines 146 and 210*a* to 210*d*.

ALTERNATE EMBODIMENT 300

Figure 6:
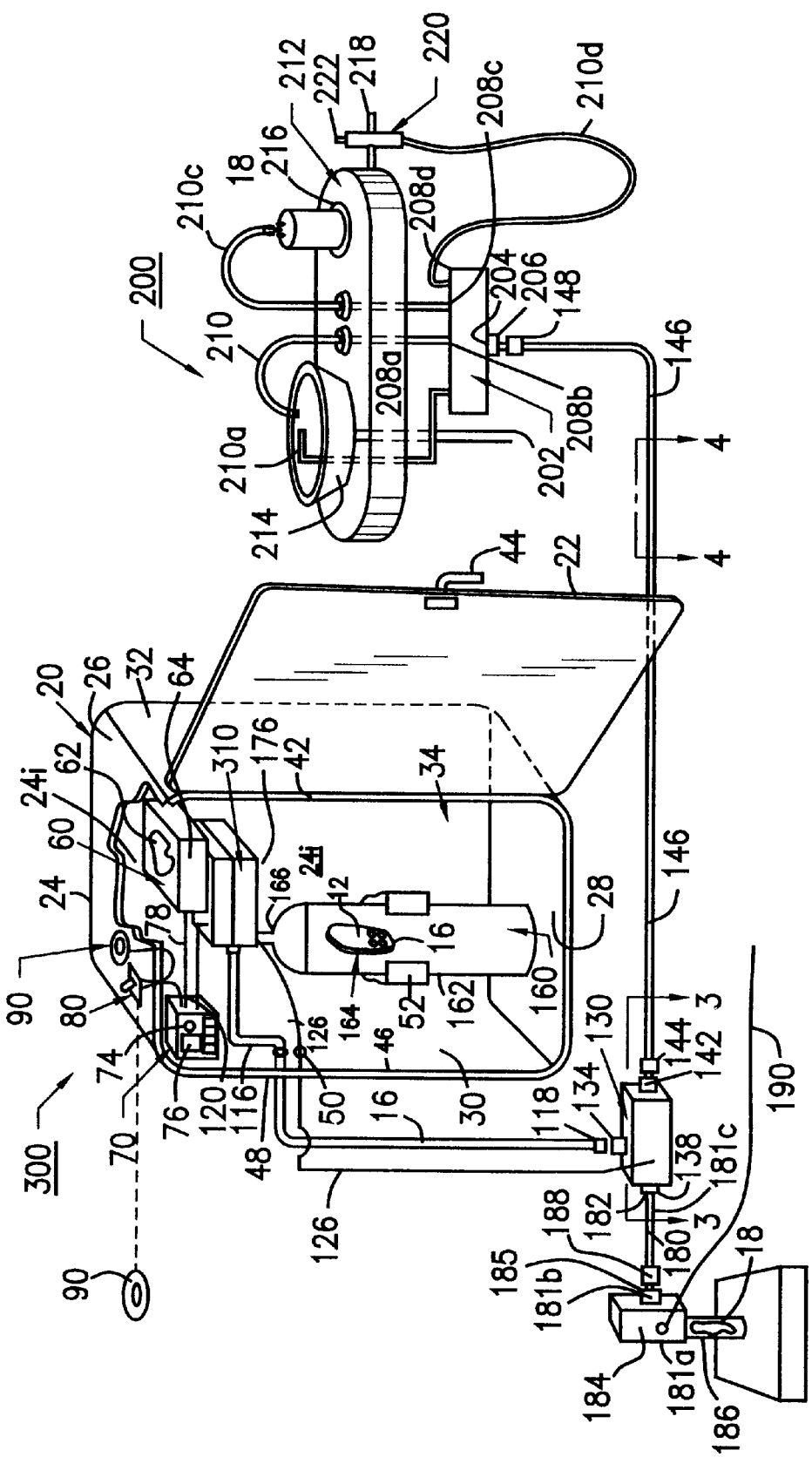
FIG. 6 is a front perspective view of the asepsis dispenser apparatus of an alternate embodiment of the present invention showing the major component parts contained therein, and in operational use to cleanse and sanitize a dental water system and its water transfer service lines.
Figure 7A:
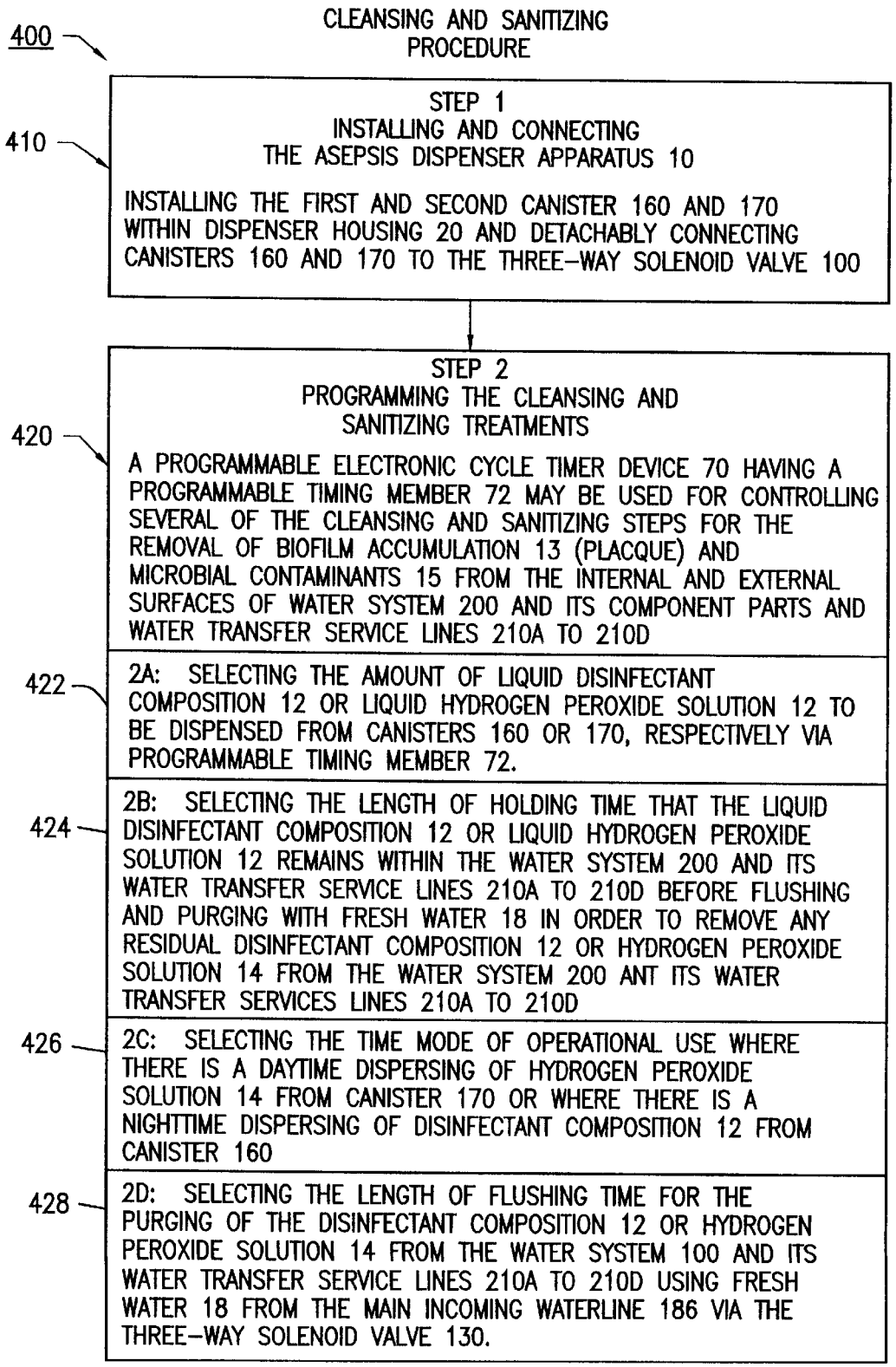
FIG. 7A is a block diagram of the cleansing and sanitizing procedure for the removal of biofilm accumulation and the destruction of pathogenic and non-pathogenic microorganisms within the water system and its water transfer service lines showing the steps of installing and connecting the asepsis dispenser apparatus, and programming the cleansing and sanitizing treatments.
Figure 7B:
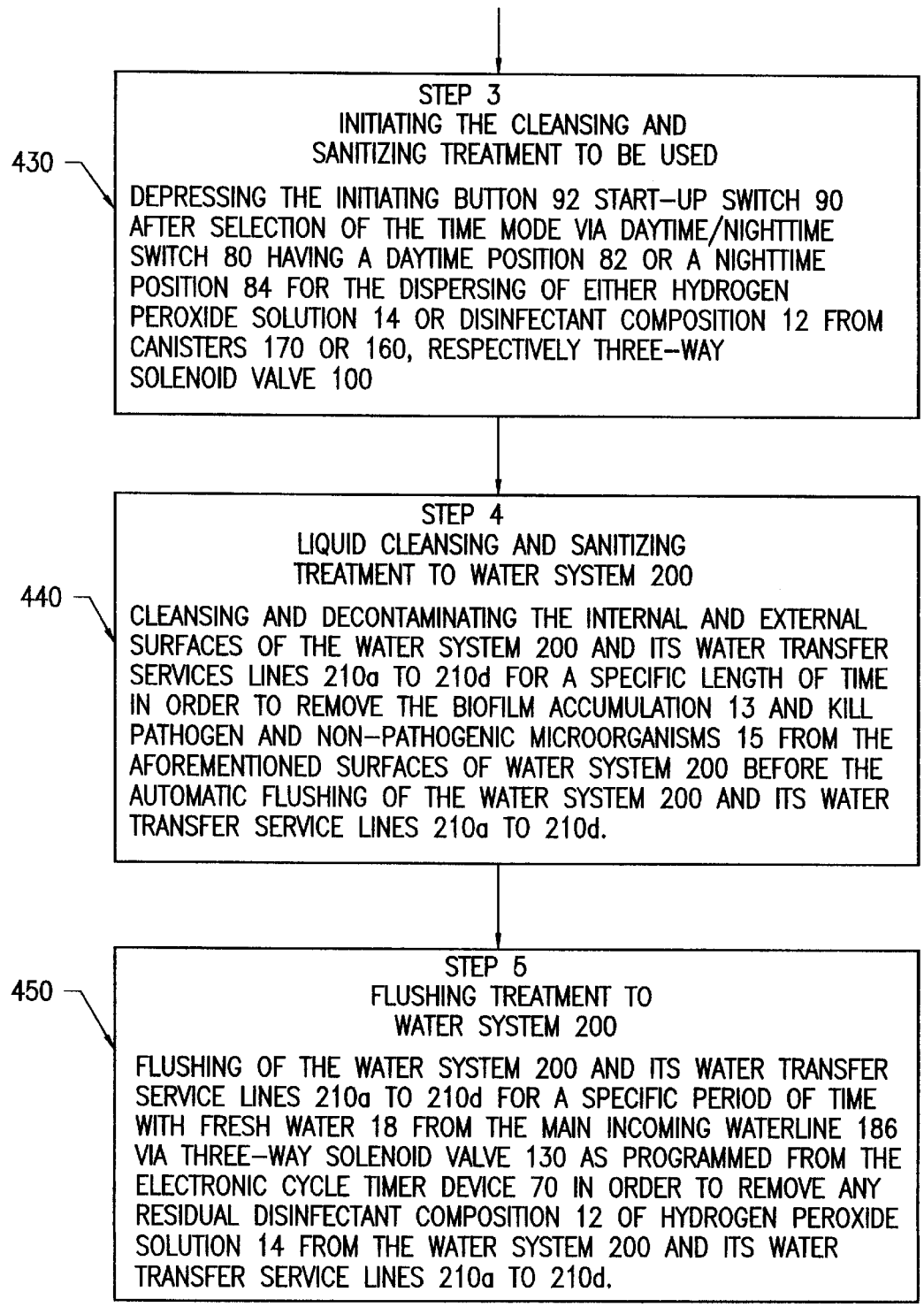
FIG. 7B is a block diagram of the cleansing and sanitizing procedure for the removal of biofilm accumulation and the destruction of pathogenic and non-pathogenic microorganism within the water system and its water transfer service lines showing the steps of initiating the cleansing and sanitizing treatment to be used, and the liquid cleansing and sanitizing treatment to water system 200 and the flushing treatment to water system 200 and its water transfer service lines 210a to 210d.

Asepsis dispenser apparatus 300 of the alternate embodiment of the present invention is depicted in detail by FIG. 6 of the drawings. All aspects of the asepsis dispenser apparatus 300 of the alternate embodiment are the same as the asepsis dispenser apparatus 10 of the preferred embodiment, except for the replacement of the three-way solenoid valve 100 with a single dispersement two-way solenoid valve 310 for detachably connecting to a single canister 160 or 170 having disinfectant composition 12 or flavored hydrogen peroxide solution 14, respectively, therein. In all other respects, asepsis dispenser apparatus 300 of the alternate embodiment functions and operates in use in the same manner as the asepsis dispenser apparatus 10 of the preferred embodiment in order to cleanse and sanitize the water system 200 and its water transfer service lines 146 and 210*a* to 210*d*, as previously described.

OPERATION OF THE PRESENT INVENTION

The asepsis dispenser apparatus 10 of the present invention is independent of the power supply and air supply of the dental/medical facility. The pressurized aerosol canisters 160 and 170 are pre-filled at an off-site location with the disinfectant composition 12 and flavored or unflavored hydrogen peroxide solution 14, respectively; and both canisters 160 and 170 being pressurized with compressed air 16 (similar to the typical spray paint can). Canisters 160 and 170 are disposable and are also safe to store and use as needed. The liquid disinfectant composition 12 and hydrogen peroxide solution 14 are released into the water system 200 and its water transfer lines 146 and 210*a* to 210*d* under pressure which will not disrupt or cause failure of valves, fittings, switches and tubing within the water system 200 being cleansed and sanitized. Apparatus 10 is permanently located near the water system 200 and the main water supply inlet line 186 of the dental/medical facility. Apparatus 10 can preferably be located close to the incoming water source 18 of the main water supply inlet 186, as shown in FIG. 1 of the drawings, of the dental/medical facility such that the dispenser housing 20 can be placed on the floor, on the wall, under a counter top or in a supply closet for the convenience of the practitioner. The dispenser housing 20 of the asepsis dispenser apparatus 10 and its external component parts are designed to be easily self-installed by the doctor, practitioner and/or staff using a minimum amount of tools for the installation of the housing 20 and the external component parts. The start-up switch 90 having an initiating sequence button 92 can be placed on the dispenser housing 20 or the start-up switch 90 can be wired remotely for the convenience of the practitioner.

The pressurized aerosol canisters 160 and 170 are then detachably connected via canister holding clips 52 and 54, respectively, on the interior rear wall 24*i* of dispenser housing 20. Canister 160 is then connected to the three-way solenoid valve 100 such that the connecting member 169 of nozzle opening 168 is detachably connected to the quick disconnect female coupling 104 of the first inlet opening 102 of three-way solenoid valve 100. Canister 170 is also then connected to the three-way solenoid valve 100 such that the connecting member 179 of nozzle opening 178 is detachably connected to the quick disconnect female coupling 108 of the second inlet opening 106 of three-way solenoid valve 100.

Next, the outlet transfer line 116 at one end 117*a*, as shown in FIGS. 1 and 2*a*, having the quick disconnect male coupling 114 thereon, is detachably connected to the quick disconnect female coupling 112 of the outlet opening 110 of three-way solenoid valve 100. Outlet transfer line 116 at the other end 117*b*, having the quick disconnect male coupling 118 thereon, is detachably connected to the quick disconnect female coupling 134 of the first inlet opening 132 of the three-way solenoid valve 130. Inlet water transfer line 180 at one end, 181*c* is detachably connected to the quick disconnect female coupling 138 of the second inlet opening 136 of three-way solenoid valve 130. Inlet water transfer line 180 at the other end having the quick disconnect male coupling 188 thereon, is detachably connected (to the other end 181*b* of automatic ball valve 184) to the quick disconnect female coupling 185 of automatic ball valve 184.

The last assembly step is connecting the water transfer line 146 to the three-way solenoid valve 130 and to the manifold member 202 of water system 200. Water transfer line 146 at one end, having quick disconnect male coupling 144 thereon, is detachably connected to the quick disconnect female coupling 142 of the outlet opening 140 of the three-way solenoid valve 130. Water transfer line at the other end, having quick disconnect male coupling 148 thereon, is detachably connected to the quick disconnect female coupling 206 of the inlet opening 204 of manifold member 202.

Both solenoid valves 100 and 130 are powered by the 9 volt battery 66 or other power supply (AC or DC). There is no need to use any other electrical connections nor is there any need to use the compressor air at the dental/medical facility in operating the asepsis dispenser apparatus 10 of the present invention. The dispenser housing 20 houses the necessary electrical components including solenoid valve 100, 9 volt battery 166, electronic cycle timer device 70, daytime/nighttime switch 80, start-up switch 90 and low voltage electrical lines 78, 86, 96, 120 and 126 for the electrical operation of asepsis dispenser apparatus 10.

Asepsis dispenser apparatus 10 is now completely assembled and in an operational mode, as shown in FIG. 1 of the drawings. The practitioner and/or staff now programs the electronic cycle timer device 70 via the programmable timing member 72 and selector knob 74. Selector knob 74 is used for selecting the output functions to be programmed by the programmable timing member 72, including the output functions of volume of disinfectant compositions 12 or 14 to be dispensed from canisters 160 or 170, respectively, and the time function for disinfectant compositions 12 and 14 to be dispensed for cleansing and sanitizing the water system 200 and its water lines before flushing with fresh water 18 from the main water supply line 186. Programmable timing member 72 is used for programming the specific volume amount of disinfectant (composition) solutions 12 or 14 used in cleansing and sanitizing the water system 200 and its water transfer lines; and the specific length of time (time period) that the disinfectant solutions 12 or 14 remain in the water system 200 and its water transfer lines before flushing by fresh water 18 from the main water supply line 186. This aforementioned time period is set by the programmable timing member 72 via keyboard 73 where a start-up time is set (at e.g. 10:00 P.M.) and a finishing time is set (at e.g. 6:00 A.M.) giving a cleansing and sanitizing time period of 8 hours for the nighttime duration; and a daytime duration time period is set (e.g. 5 minutes) having no specific start-up or finish times. The daytime duration is dependant upon setting of the daytime/nighttime switch 80 to the daytime position 82 and the initiation of cleansing and sanitizing by the practitioner via start-up switch 90 after each patient visit. Each of the aforementioned output functions of volume and time periods are visually displayed via the visual display screen 76 of cycle timer device 70 for the practitioner's control.

In operation, the asepsis dispenser apparatus 10 is in either a daytime mode of cleansing and sanitizing between patient visits or a nighttime mode of cleansing and sanitizing the biofilm and microbial contaminants on contaminated internal and external surfaces wherein the nighttime mode cycles before each daily operation (each day) of the dental/medical facility being utilized. For example, if the practitioner has finished with his/her patients at the end of the work day (e.g. 5:00 P.M.), the practitioner and/or staff initiates the nighttime mode of operation by positioning the daytime/nighttime switch 80 to the nighttime setting/position 84 and then depressing the initiating button 92 of start-up switch 90. This starts the nighttime operational mode to begin at, e.g. 10:00 P.M., such that the three-way solenoid valve 100 allows the disinfectant composition 12 from canister 160 to flow through nozzle opening 168 and first inlet opening 102 of canister 160 and three-way solenoid valve 100, respectively. Solenoid valve 100 has electronically blocked-off nozzle opening 178 of canister 170 via stop member 122 in order to allow the disinfectant composition 12 to dispense approximately 4.4 ounces (oz.) (for approximately a one (1) minute duration) of the disinfectant liquid solution 12 under pressure through outlet opening 110 and outlet transfer line 116, as shown in detail by FIG. 2b of the drawings. Simultaneously, three-way solenoid valve 130 has rotated and positioned its internal rotatable valve member 152 at its second valve open position 156 in order to allow the flow of the disinfectant liquid composition 12 under pressure to continue to flow from outlet transfer line 116 through first inlet opening 132 and outlet opening 140 of three-way solenoid valve 130, as shown in detail by FIG. 3b of the drawings. In this manner, disinfectant composition 12 flows through water transfer line 146, the water system 200 and its water transfer service lines 210a to 210d for cleansing and sanitizing the biofilm and microbial contaminants therein. The main water supply 186 of fresh water 18 has been shut-off to the water system 200 and its component parts, as shown in FIG. 3b.

After the 4.4 oz. of disinfectant composition 12 has been dispensed under pressure, the pressurized cleansing and sanitizing disinfectant solution 12 has entered the water transfer line 146, the water system 200, its component parts 202, 214, 216 and 222, and its water transfer service lines 210a to 210d, so that the disinfectant solution 12 has purged the entire water system 200 of all residual water 18 that had previously filled the water system 200 before cleansing and sanitizing. Residual water 18 is allowed to escape by removing from water system 200 all of the handpieces 222 and drills and by also manually or mechanically holding the air-water syringes open.

After the 4.4 oz. of disinfectant composition 12 has been dispensed for the one minute time period, solenoid valve 100 is moved to a closed/shut-off position where stop member 122 closes off outlet opening 110 from any further dispensing of disinfectant composition 12 from canister 160, as depicted in detail by FIG. 2c of the drawings, via the electronic cycle timer device 70; and solenoid valve 130 remains in a closed position for preventing any water 18 from the main incoming water supply line 186 from entering into the water system 200. The main water source 18 from water supply line 186 is electrically activated by automatic ball valve 184 via electrical line 190 (or manually) and is also automatically shut-off at the end of the work day.

The aforementioned sequence is controlled by electronic cycle timer device 70 via the programmable timing member 72 as programmed by the practitioner and/or staff. The volume of disinfectant composition 12 has been previously calibrated to deliver the correct volume of disinfectant composition 12 to the water system 22 and its water transfer service lines 210a to 210d, as previously described. The disinfectant composition 12 remains in the water system 200 and its water transfer service lines 210a to 210d for at least 8 hours (as programmed). Then, at e.g., 6:00 A.M. the water system 200 and its water transfer service lines 210a to 210d are automatically purged with fresh water 18 from the main incoming water line 186 for approximately 3 minutes of time. This sequence of events are achieved by the electronic timer device 70 repositioning the internal rotatable valve member 152 of the three-way solenoid valve 130 to its first valve open position 154 and opening of the automatic ball valve 184 to allow purging of fresh water 18 from the main incoming water line 186. The disinfectant composition 12 can remain in the water system 200 and its water transfer service lines 210a to 210d for extended periods of time, a week to a month without, harming or causing any problems to the water system 200 and its component parts at the dental/medical facility.

Figure 4:
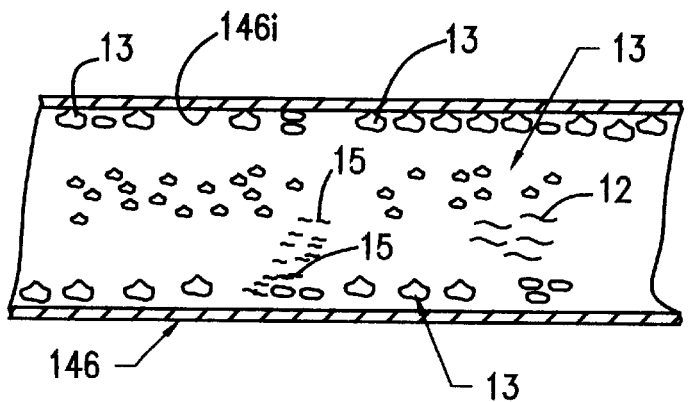
FIG. 4 is an enlarged cross-sectional view of the water inlet line to the dental water system taken along lines 4—4 of FIG. 1 showing the cleansing and sanitizing action of the disinfectant composition for removing the biofilm accumulation and sanitizing microbial contaminants on the interior surface of the water inlet line.

In the daytime mode of operation using the asepsis dispenser apparatus 10, the practitioner and/or staff change the daytime/nighttime switch 80 to the daytime setting/position 82 which allows the three-way solenoid valve 100 to receive the flavored hydrogen peroxide solution 14 under pressure from canister 170. The hydrogen peroxide solution 14 flows from the nozzle opening 178 through second inlet opening 106 of solenoid valve 100 to the outlet opening 110 and transfer line 116. Solenoid valve 100 has electronically blocked-off nozzle opening 168 of canister 160 via stop member 122 in order to allow the dispensing of the flavored or unflavored hydrogen peroxide solution 14 under pressure from canister 170 for a predetermined amount of time (e.g. 20 seconds to 30 seconds for dispensing approximately 2 oz. of hydrogen peroxide solution 14) through outlet opening 110 and outlet transfer line 116, as shown in detail by FIG. 2a of the drawings. Simultaneously, three-way solenoid valve 130 has rotated and positioned its internal rotatable valve member to its second valve position 156 in order to allow the flow of the flavored hydrogen peroxide solution 14 under pressure to continue to flow from outlet transfer line 116 through first inlet opening 132 and outlet opening 140 of three-way solenoid valve 130, as shown in detail by FIG. 3b of the drawings. In this manner, the flavored hydrogen peroxide solution 14 flows through water transfer line 146, the water system 200 and its water transfer service lines 210a to 210d for cleansing and sanitizing the biofilm and microbial contaminants therein after each patient visit. The above sequence of flow of the flavored hydrogen peroxide solution 14 is initiated by depressing initiating sequence button 92 of start-up switch 90. This daytime cleansing and sanitizing procedure is performed in order to prevent the back flow of oral pathogenic microorganisms into the water transfer service lines 210a to 210d and water transfer line 146 after treatment of each patient, as this microbial contamination 15 has been shown to occur between patient usages of the water system 200. This microbial contamination 15 can penetrate several feet into the water transfer line 146 and the water transfer service lines 210a to 210d, such that asepsis dispenser apparatus 10 has also been designed to purge or pulse the lines with the flavored hydrogen peroxide solution 14 between patient visits in order to cleanse, destroy and kill the harmful biofilm 13 and microbial contaminants 15, as shown in FIG. 4 of the drawings.

The remaining operational and flow sequences of the hydrogen peroxide solution 14 are exactly the same as described for the flow events shown for dispensing of the disinfectant composition 12 and purging by fresh water 18 from the main water supply line 186 in order to cleanse and sanitize the water system 200 and its water transfer lines. If all of the hydrogen peroxide solution 14 is accidentally not flushed, the patient will not experience any unpleasant after taste with the flavored hydrogen peroxide solution 14 when rinsing water 18 from water transfer service line 210c, as shown in FIG. 1.

A recommendation for typical operational use for dispensing disinfectant composition 12 via the asepsis dispenser apparatus 10 would be cleaning every night for 2 to 10 hours with the disinfectant composition 12 after the water system 200 has been shut down for the day. The exact time requirements for nighttime cleansing and sanitizing of each facility may differ depending on water quality of the source water, age of the water systems 200 involved, and the amount of biofilm accumulation (plaque) 13 within each of the water lines to be cleansed, and may be performed as a matter of standard operating procedure for cleaning all water systems.

ADVANTAGES OF THE PRESENT INVENTION

Accordingly, an advantage of the present invention is that it provides for an asepsis apparatus for dispensing a disinfectant composition for the cleaning and decontamination of the biofilm and microbial contaminants within water systems and to the water and air lines used in medical and dental facilities.

Another advantage of the present invention is that it provides an asepsis apparatus for safely and automatically supplying a disinfectant composition which, when applied to the contaminated internal surfaces of the water system and its air and water lines/tubes, the disinfectant will kill or inactivate viruses, bacteria, funguses, and parasites on contact.

Another advantage of the present invention is that it provides an asepsis apparatus that is adaptable to any new or used dental chair system by any manufacturer such that the small and unobtrusive asepsis apparatus can be easily and quickly installed by the practitioner.

Another advantage of the present invention is that it provides an asepsis apparatus that operates on a 9 volt battery or other power supply (AC or DC) having no electrical connections (to a wall electrical outlet) if needed.

Another advantage of the present invention is that it provides an asepsis apparatus that is easy to use and there is no servicing required, such that by a touch of a button the asepsis apparatus will initiate a self-contained timer which will deliver a correct volume of disinfectant composition/solution to the dental water system and its air and water lines for an appropriate cleaning and decontamination procedure.

Another advantage of the present invention is that it provides an asepsis apparatus for automatically supplying a predetermined amount of disinfectant solution for the decontamination and cleaning of the dental equipment (i.e. water system and its water and air lines, during the non-working hours (night time) at the dental facility.

Another advantage of the present invention is that it provides an asepsis apparatus that prevents back flow from dental handpieces, syringes, and back pressure vapor contamination from suction lines, such that the resultant water and air purity is well below the recommended 200 CFU/liter, established by the Centers for Disease Control and Prevention, after the cleaning and decontamination by the disinfectant composition which chemically disinfects, filters and scrubs the biofilm from the water and air lines of any dental water system.

Another advantage of the present invention is that it provides an asepsis apparatus that includes a self-charging system being easily applied to the dental water system and where no leaking of the asepsis apparatus occurs when left unattended.

Another advantage of the present invention is that it provides a asepsis apparatus having disposable components therein and still operates at a low cost of utilization for parts and disinfectant solution.

Another advantage of the present invention is that it provides an asepsis apparatus that has a low cost of manufacturing and having a minimal amount of components; and is durable, safe and reliable in operation without causing damage to the water system and its air and water lines being cleaned and decontaminated.

A further advantage of the present invention is that it provides an asepsis apparatus that may be mass produced in an automated and economical manner and is readily affordable by the practitioner.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. An asepsis dispenser apparatus for dispensing disinfectant solutions for cleansing and decontaminating the contaminated surfaces of dental, food or medical equipment, said equipment being connected to a water source by a water inlet line, comprising:

a) a housing having an interior compartment for holding in place first and second storage canisters in said housing;

b) said first storage canister for containing a first disinfectant composition;

c) said second storage canister for containing a second disinfectant composition;

d) first valve means connected directly to both of said first and second storage canisters within said housing and being selectively operable between first and second canisters for communicating with said first and second disinfectant compositions for cleaning and decontaminating the dental, food or medical equipment;

e) second valve means connected to said first valve means; said second valve means for controlling the supply of water from the water source to a water inlet line connected to said dental, food or medical equipment;

f) timing controller means for opening and closing said first and second valve means to control said first and second storage canisters to supply said first disinfectant composition or said second disinfectant composition to the contaminated surfaces; and g) power supply means for supplying electrical power to said first and second valve means and to said timing controller means.

2. An asepsis dispenser apparatus in accordance with claim 1, wherein said first valve means includes a first three-way solenoid valve.

3. An asepsis dispenser apparatus in accordance with claim 1, wherein said second valve means includes a second three-way solenoid valve.

4. An asepsis dispenser apparatus in accordance with claim 1, wherein said timing controller means includes a programmable electronic cycle timer device having a programmable timing controller member, a keyboard and a selector knob.

5. An asepsis dispenser apparatus in accordance with claim 1, wherein said power supply means includes a 9 volt battery, or a power supply plugged into an outlet, or is hard wired.

6. An asepsis dispenser apparatus in accordance with claim 1, further including a selector switch for selecting a daytime or nighttime mode of operation.

7. An asepsis dispenser apparatus in accordance with claim 1, further including a start-up switch for initiating the operational use of said asepsis dispenser apparatus.

8. An asepsis dispenser apparatus in accordance with claim 1, wherein said housing is made of plastic or metal for ease of cleaning, or is built into a dental chair or closet control panel on the dental chair, or is remotely located.

9. An asepsis dispenser apparatus in accordance with claim 1, wherein said first and second storage canisters are pressurized with sterile compressed air, carbon dioxide, nitrogen or helium.

10. An asepsis dispenser apparatus for dispensing disinfectant solutions for cleansing and decontaminating the contaminated surfaces of dental, food or medical equipment, said equipment being connected to a water source by a water inlet line, comprising:

a) a housing having an interior compartment for holding in place a storage canister in said housing;

b) said storage canister for containing a disinfectant composition;

c) first valve means connected directly to said storage canister within said housing and being operable with said storage canister for communicating with said disinfectant composition for cleaning and decontaminating the dental, food or medical equipment;

d) second valve means connected to said first valve means; said second valve means for controlling the supply of water from the water source to a water inlet line connected to said dental, food or medical equipment for flushing said disinfectant position and for normal use;

e) timing controller means for opening and closing said first and second valve means to control said storage canister to supply said disinfectant composition to the contaminated surfaces; and f) power supply means for supplying electrical power to said first and second valve means and to said timing controller means.

11. An asepsis dispenser apparatus in accordance with claim 10, wherein said first valve means includes a first three-way solenoid valve.

12. An asepsis dispenser apparatus in accordance with claim 10, wherein said second valve means includes a second three-way solenoid valve.

13. An asepsis dispenser apparatus in accordance with claim 10, wherein said timing controller means includes a programmable electronic cycle timer device having a programmable timing controller member, a keyboard and a selector knob.

14. An asepsis dispenser apparatus in accordance with claim 10, wherein said power supply means includes a 9 volt battery, or an AC or DC power supply.

15. An asepsis dispenser apparatus in accordance with claim 10, further including a selector switch for selecting a daytime or nighttime mode of operation.

16. An asepsis dispenser apparatus in accordance with claim 10, further including a start-up switch for initiating the operational use of said asepsis dispenser apparatus.

17. An asepsis dispenser apparatus in accordance with claim 10, wherein said housing is made of plastic or metal for ease of cleaning, or is built into the dental chair, or is remotely located.

18. An asepsis dispenser apparatus in accordance with claim 10, wherein said storage canister is pressurized with sterile compressed air, carbon dioxide, nitrogen or helium.

* * * * *